(12) United States Patent
Ueda et al.

(10) Patent No.: US 8,367,874 B2
(45) Date of Patent: Feb. 5, 2013

(54) PROCESS FOR PRODUCING 2-(1-HYDROXYALKYL)CYCLOALKANONE

(75) Inventors: Junko Ueda, Wakayama (JP); Yoshiharu Ataka, Wakayama (JP)

(73) Assignee: Kao Corporation, Tokyo (JP)

( * ) Notice: Subject to any disclaimer, the term of this patent is extended or adjusted under 35 U.S.C. 154(b) by 219 days.

(21) Appl. No.: 12/810,609

(22) PCT Filed: Dec. 22, 2008

(86) PCT No.: PCT/JP2008/073315
§ 371 (c)(1),
(2), (4) Date: Sep. 8, 2010

(87) PCT Pub. No.: WO2009/084504
PCT Pub. Date: Jul. 9, 2009

(65) Prior Publication Data
US 2011/0009673 A1    Jan. 13, 2011

(30) Foreign Application Priority Data
Dec. 28, 2007    (JP) ................................ 2007-340892

(51) Int. Cl.
*C07C 45/64*    (2006.01)
(52) U.S. Cl. ...................................................... 568/343
(58) Field of Classification Search ................ 568/343, 568/345
See application file for complete search history.

(56) References Cited

U.S. PATENT DOCUMENTS

| 7,161,042 B2 | 1/2007 | Clissold et al. |
| 7,227,044 B2 | 6/2007 | Mine |

FOREIGN PATENT DOCUMENTS

| JP | 2001 213837 | 8/2001 |
| JP | 2004 217619 | 8/2004 |
| JP | 2005 255646 | 9/2005 |

OTHER PUBLICATIONS

Extended European Search Report issued on Dec. 12, 2011 in the corresponding European Application No. 08868514.4.

*Primary Examiner* — Sikarl Witherspoon
(74) *Attorney, Agent, or Firm* — Oblon, Spivak, McClelland, Maier & Neustadt, L.L.P.

(57) ABSTRACT

The present invention relates to a process for producing a 2-(1-hydroxyalkyl)cycloalkanone which includes the steps of (i) continuously mixing a cycloalkanone and an alkyl aldehyde in the water and a base catalyst to form a reaction system and allow both the compounds to react with each other; (ii) continuously withdrawing a reaction mixture produced in the step (i) out of the reaction system while allowing the step (i) to proceed; and (iii) adding an additional amount of water containing the base catalyst to the reaction system to maintain a constant concentration of the base catalyst and/or a constant amount of water in the reaction system while allowing the step (ii) to proceed.

7 Claims, 1 Drawing Sheet

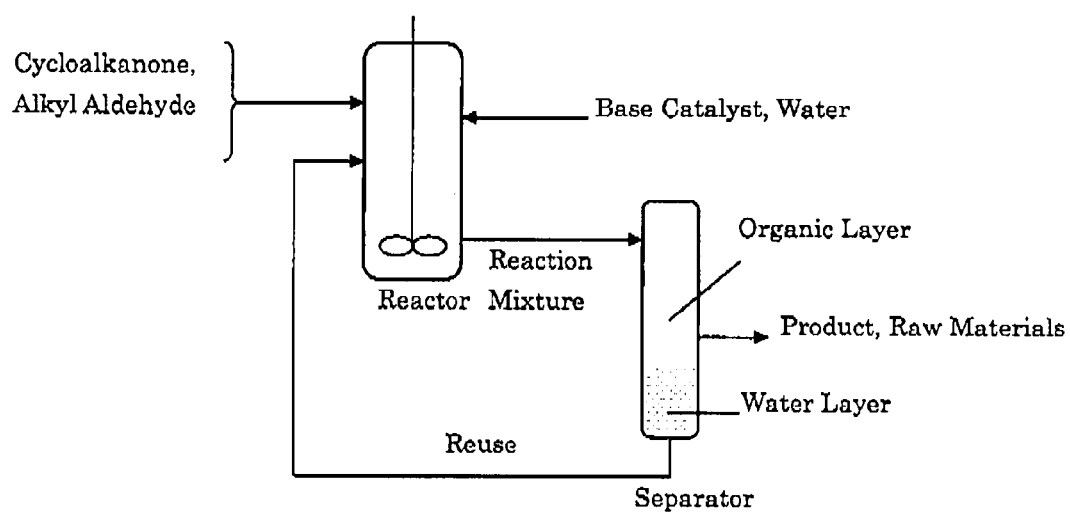

PROCESS FOR PRODUCING 2-(1-HYDROXYALKYL)CYCLOALKANONE

FIELD OF THE INVENTION

The present invention relates to a process for producing 2-(1-hydroxyalkyl)cycloalkanones.

BACKGROUND OF THE INVENTION 2-(1-Hydroxyalkyl)cycloalkanones are useful substances as an intermediate product for synthesis of physiologically active substances or perfume materials. There are conventionally known the methods for producing the 2-(1-hydroxyalkyl)cycloalkanones in which a cycloalkanone and an alkyl aldehyde are subjected to aldol condensation reaction in the presence of water and a base catalyst in a batch mariner (refer to Patent Documents 1 to 3). However, in these batch-type methods, it is required to neutralize the resulting base catalyst aqueous solution with an acid and recover water and residual cycloalkanone contained in an organic layer of the resulting reaction mixture by distillation whenever each reaction has been completed. Thus, the conventional methods are still unsatisfactory in productivity. Also, in Patent Document 3, it is suggested that a water layer formed in an aldol condensation reaction can be reused. However, in this method, in order to reuse the water layer, it is required to once neutralize the resulting reaction mixture by adding an acid thereto and separate the thus neutralized reaction mixture into the water layer and an organic layer to remove the organic layer from the water layer, followed by adding a base catalyst to the thus separated water layer to render the water layer basic. For this reason, in the method described in Patent Document 3, there tends to occur such a problem that the raw materials used for the aldol condensation reaction are deteriorated in solubility in the water layer owing to increased content of the neutralized salt therein, so that the yield of the aimed compound is reduced as the water layer is thus reused repeatedly. Therefore, in the above method, in order to prevent reduction in yield of the aimed compound, the times of reuse of the water layer must be limited, and further a large amount of water which is no longer reusable must be discarded. In addition, the method also tends to have the problem that the cycloalkanone dissolved in the water layer causes a loss thereof.

Patent Document 1: JP-A 56-147740
Patent Document 2: JP-A 2001-335529
Patent Document 3: JP-A 2004-217619

BRIEF DESCRIPTION OF THE DRAWING

FIG. 1 is an explanatory view conceptually showing an example of the production process according to the present invention.

SUMMARY OF THE INVENTION

The present invention relates to a process for continuously producing a 2-(1-hydroxyalkyl)cycloalkanone while suppressing reduction in a yield thereof.

In view of the above conventional problems, the present inventors have found such a process for producing a 2-(1-hydroxyalkyl)cycloalkanone in which when conducting the step of dropping and mixing a mixed solution of a cycloalkanone and an alkyl aldehyde in an aqueous solution of a base catalyst while withdrawing the resulting reaction mixture out of the reaction system, an additional amount of water containing the base catalyst is added to the reaction system in order to maintain a constant concentration of the base catalyst and/or a constant amount of water in the reaction system to thereby allow an aldol condensation reaction between the cycloalkanone and the alkyl aldehyde to proceed in a continuous manner. In addition, the present inventors have found that in order to carry out the aldol condensation reaction in a continuous manner, when separating the reaction mixture withdrawn out of the reaction system into an organic layer and a water layer and then recovering and reusing the thus separated water layer in the reaction system, it is required to continuously add the base catalyst to the reaction system to compensate a loss of the base catalyst because the base catalyst tends to be converted into a neutralized salt by the reaction with a small amount of an alkyl carboxylic acid contained in the alkyl aldehyde as a raw material, and therefore deactivated. Further, the present inventors have found that since the concentration and amount of the base catalyst in the reaction system can be kept constant by continuously adding the water containing the base catalyst to the reaction system, it is possible to suppress decrease in the reaction rate as well as deactivation of the base catalyst, so that the aldol condensation reaction is allowed to proceed substantially semi-permanently and the 2-(1-hydroxyalkyl)cycloalkanone as the aimed compound can be produced with a high efficiency in a continuous manner.

Thus, the present invention relates to a process for producing a 2-(1-hydroxyalkyl)cycloalkanone by subjecting a cycloalkanone and an alkyl aldehyde to aldol condensation in the presence of water and a base catalyst, which includes the following steps (i) to (iii):

Step (i): continuously mixing the cycloalkanone and the alkyl aldehyde in the water and the base catalyst to form a reaction system and allow both the compounds to react with each other;

Step (ii): continuously withdrawing a reaction mixture produced in the step (i) out of the reaction system while allowing the step (i) to proceed; and Step (iii): adding an additional amount of water containing the base catalyst to the reaction system to maintain a constant concentration of the base catalyst and/or a constant amount of water in the reaction system while allowing the step (ii) to proceed.

Effect of the Invention

In accordance with the production process of the present invention, the 2-(1-hydroxyalkyl)cycloalkanone can be continuously produced while suppressing reduction in a yield thereof.

DETAILED DESCRIPTION OF THE INVENTION

FIG. 1 is an explanatory view conceptually showing a preferred embodiment of the production process according to the present invention. In FIG. 1, a reactor serves for subjecting a cycloalkanone and an alkyl aldehyde which are continuously added thereto and mixed therein, to aldol condensation reaction in the presence of water and a base catalyst. Thus, the reactor is continuously supplied with the cycloalkanone and the alkyl aldehyde as well as the water containing the base catalyst. The reaction mixture obtained in the reactor is continuously withdrawn therefrom and introduced into a separator in which the reaction mixture is then separated into an organic layer and a water layer. The respective steps of the production process according to the present invention are described in detail below.

[Step (i)]

In the step (i), the cycloalkanone and the alkyl aldehyde are continuously added to the reactor in the presence of water and the base catalyst to form a reaction system. In the reaction system, the cycloalkanone and the alkyl aldehyde are subjected to aldol condensation reaction. The reactor used in the step (i) is not particularly limited as long as the reactor is provided with feed ports for the cycloalkanone, the alkyl aldehyde, water, the base catalyst or the like, a discharge port for withdrawing the reaction mixture therethrough, and other ports for the water layer reused, etc. For example, as the reactor, there may be used a reactor of a stirring vessel type.

The temperature used in the above reaction is not particularly limited, and is preferably from −5 to 40° C. and more preferably from −5 to 30° C., for example, for the purposes of preventing solidification of the water layer and suppressing production of by-products such as a dimer of the cycloalkanone. Also, the pressure used in the aldol condensation reaction is preferably from 10 kPa to 1 MPa in terms of an absolute pressure, and more preferably from 50 to 300 kPa and still more preferably from 80 to 120 kPa from the viewpoint of inexpensiveness of apparatuses used thereunder.

<<Cycloalkanone>>

The cycloalkanone used in the present invention includes cycloalkanones having 4 to 8 carbon atoms. Among these cycloalkanones, preferred are cyclopentanone and cyclohexanone, and more preferred is cyclopentanone.

<<Alkyl Aldehyde>

As the alkyl aldehyde used in the present invention, those aldehydes preferably containing an alkyl group having 1 to 15 carbon atoms, more preferably an alkyl group having 1 to 8 carbon atoms and still more preferably an alkyl group having 3 to 5 carbon atoms are preferred, and the aldehyde containing a straight-chain alkyl group having 4 carbon atoms is most preferred. The aldehydes containing an alkyl group having 3 to 5 carbon atoms include butyraldehyde, isobutyraldehyde, valeraldehyde, isovaleraldehyde and hexylaldehyde, and the aldehyde containing a straight-chain alkyl group having 4 carbon atoms is valeraldehyde.

In order to produce the aimed compound from the cycloalkanone and the alkyl aldehyde with a good yield and separate the reaction mixture into the organic layer and the water layer without neutralizing the reaction mixture with an acid, the cycloalkanone to be reacted is preferably added in an excessive amount relative to the alkyl aldehyde. On the other hand, in view of preventing deterioration in productivity owing to recovery of a surplus amount of the cycloalkanone, etc., the amount of the cycloalkanone added is preferably from 2 to 6 mol, more preferably from 3 to 5 mol and still more preferably from 3 to 4 mol per 1 mol of the alkyl aldehyde.

The cycloalkanone and the alkyl aldehyde may be supplied by (i) the method of previously mixing the cycloalkanone and the alkyl aldehyde, or (ii) the method of adding the cycloalkanone and the alkyl aldehyde separately from each other. Among these methods, preferred is the method (i).

<<Base Catalyst>>

The base catalyst used in the present invention is not particularly limited. Examples of the suitable base catalyst include those compounds represented by the following formula (7).

$$M(OH)_m \quad (7)$$

In the formula (7), M is an alkali metal such as Li, Na and K, or an alkali earth metal such as Mg, Ca and Ba. Among these metals, in order to attain a good reaction efficiency, preferred are alkali metals. The symbol m is an integer of 1 or 2. Among the base catalysts represented by the above formula (7), preferred are sodium hydroxide, potassium hydroxide and calcium hydroxide, more preferred are sodium hydroxide and potassium hydroxide, and still more preferred is sodium hydroxide.

The amount of the base catalyst used in the reaction system is preferably adjusted to from 0.005 to 0.5 mol, more preferably from 0.01 to 0.1 mol and still more preferably from 0.02 to 0.08 mol per 1 mol of the alkyl aldehyde added in terms of an amount per unit time, from the viewpoints of suppressing occurrence of side reactions and enhancing the reaction rate.

<<Water>>

The amount of water being present in the reaction system is important to determine a concentration of the base catalyst in the reaction system. From the viewpoint of preventing production of by-products such as dimers of the alkyl aldehyde and the cycloalkanone and high-boiling components, the amount of water being present in the reaction system is controlled such that the concentration of the base catalyst in the reaction system is preferably from 0.1 to 3% by mass, more preferably from 0.5 to 2.5% by mass and still more preferably from 0.8 to 2% by mass on the basis of a total amount of water and the base catalyst contained in the reaction system.

<<Solvent>>

The reaction between the cycloalkanone and the alkyl aldehyde may be carried out in a solvent. However, since the reaction is carried out in a two-layer system containing cycloalkanone and water, it is required to select a solvent suitable for such a two-layer reaction system. The suitable solvent is not particularly limited as long as it is inert to the aldol condensation reaction and unless it adversely affects separation and purification of the aimed compound according to the present invention. Examples of the solvent include those having a boiling point of from about 140 to about 210° C., e.g., aromatic hydrocarbon solvents such as benzene and toluene; and aliphatic hydrocarbon solvents such as nonane, decane and undecane.

The preferred 2-(1-hydroxyalkyl)cycloalkanone obtained by the aldol condensation reaction according to the present invention includes those compounds represented by the following general formula (1).

In the general formula (1), n is an integer of 1 or 2, and is preferably 1. $R^1$ is a hydrogen atom or an alkyl group having 1 to 8 carbon atoms, preferably a straight-chain or branched alkyl group having 3 to 5 carbon atoms and more preferably a straight-chain alkyl group having 4 carbon atoms.

In the aldol condensation reaction, in addition to the 2-(1-hydroxyalkyl)cycloalkanone, an alkylidene cycloalkanone which is a dehydrated product of the 2-(1-hydroxyalkyl)cycloalkanone is also produced. The dehydrated product thus produced is also useful as an intermediate product for synthesis of physiologically active substances and perfume materials similarly to the 2-(1-hydroxyalkyl)cycloalkanone.

[Step (ii)]

In the step (ii), the reaction mixture obtained in the step (i) is continuously withdrawn out of the reaction system while allowing the step (i) to proceed. The term "while allowing the step (i) to proceed" as used herein is intended to involve the condition in which the withdrawal of the reaction mixture is conducted simultaneously with initiation of the step (i), the condition in which the withdrawal of the reaction mixture is conducted during proceeding of the step (i), or the like. In the production process of the present invention, since both the continuous addition (mixing) of the cycloalkanone and the alkyl aldehyde to the reaction system and the continuous withdrawal of the reaction mixture out of the reaction system are carried out in the above-mentioned manner, the aimed compound can be continuously produced with a higher productivity as compared to batch-type processes in which each reaction must be independently and separately conducted.

The amount of the reaction mixture withdrawn is preferably adjusted such that the total amount of the cycloalkanone and the alkyl aldehyde added to the reaction system in the step (1) is substantially identical to the amount of the organic layer in the reaction mixture withdrawn. The amount of the reaction mixture withdrawn is preferably from 1 to 2.5 times, more preferably from 1 to 2 times and still more preferably from 1.2 to 2 times the total amount of the cycloalkanone and alkyl aldehyde added to the reaction system in terms of a volume ratio therebetween. When the amount of the reaction mixture withdrawn lies within the above-specified range, the aimed compound can be produced with a high yield.

[Step (iii)]

In the step (iii), an additional amount of water containing the base catalyst is added to the reaction system in order to maintain a constant concentration of the base catalyst and/or a constant amount of water in the reaction system, preferably both a constant concentration of the base catalyst and a constant amount of water in the reaction system, while allowing the step (ii) to proceed. The term "while allowing the step (ii) to proceed" as used herein is intended to involve the condition in which the addition of the water containing the base catalyst to the reaction system is conducted simultaneously with initiation of the step (ii), the condition in which the addition of the water containing the base catalyst to the reaction system is conducted during proceeding of the step (ii), or the like.

The alkyl aldehyde used in the present invention may sometimes contain an alkyl carboxylic acid as an oxidized compound of the alkyl aldehyde. The base catalyst added to the reaction system in the step (iii) is used to compensate an amount of the base catalyst consumed by the reaction with the alkyl carboxylic acid, i.e., in order to maintain a constant concentration of the base catalyst in the reaction system. The amount of the base catalyst added to the reaction system in the step (iii) may be identical to such an amount which is capable of compensating the amount of the base catalyst thus consumed. More specifically, the amount of the base catalyst added to the reaction system in the step (iii) is almost the same as the number of moles of valeric acid contained in valeraldehyde as the raw material which is determined by measuring an acid value of the valeraldehyde. Also, the amount of water added to the reaction system in the step (iii) is almost the same as the amount of water which is dissolved in the organic layer and withdrawn together with the organic layer from the reaction system.

In the present invention, it is unnecessary to supply an acid which has been conventionally needed in some cases to rapidly separate the reaction mixture into a water layer and an organic layer, so that production of a neutralized salt by the reaction between the acid and the base catalyst can be prevented. As a result, the base catalyst may be added merely in an amount enough to compensate the above amount of the base catalyst consumed by the reaction with the alkyl carboxylic acid contained in the alkyl aldehyde, which results in reduction in amount of the base catalyst to be added.

In the step (iii), the addition of the water containing the base catalyst to the reaction system may be carried out by adding an aqueous base catalyst solution prepared by previously dissolving the base catalyst in water, to the reaction system.

[Step (iv)]

In the step (iv), the reaction mixture withdrawn in the step (ii) is separated into the organic layer and the water layer, and the thus separated water layer is reused. Thus, the production process of the present invention preferably further includes the above step (iv) from the viewpoints of reducing an amount of waste water discharged and reusing the cycloalkanone contained in the water layer. The water layer separated by the separator is recycled to the reaction system and reused therein.

[Step (v)]

The production process of the present invention preferably further includes the step (v) of subjecting the organic layer separated in the step (iv) to distillation to recover the cycloalkanone contained in the organic layer and then reuse the cycloalkanone in the reaction system. In the production process of the present invention, the cycloalkanone used in an excessive amount partially remains unreacted and contained in the organic layer. Therefore, such an unreacted cycloalkanone is recovered from the organic layer by distillation and reused in the reaction system to thereby enhance a production efficiency. In the step (v), water contained in the organic layer may also be recovered therefrom and reused in the reaction system.

[Method for Production of Alkyl(3-oxo-2-alkylcycloalkyl)acetate]

An alkyl(3-oxo-2-alkylcycloalkyl)acetate represented by the following general formula (5) (hereinafter referred to merely as a "compound (5)") is a useful compound as a perfume material and a physiologically active substances, and can be obtained from the compound (1) produced by the production process of the present invention as described above.

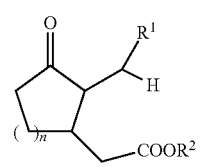

(5)

In the general formula (5), n and $R^1$ are the same as defined above, and $R^2$ is an alkyl group having 1 to 3 carbon atoms, and is preferably a methyl group.

The method for producing the compound (5) is not particularly limited. For example, the compound (5) may be produced by the following method. First, the compound (1) is subjected to dehydration reaction to obtain a 2-(alkylidene)cycloalkanone represented by the following general formula (2) (hereinafter referred to merely as a "compound (2)"). The thus obtained compound (2) is subjected to isomerization reaction in n-butanol under reflux in the presence of an aqueous acid such as hydrochloric acid and hydrobromic acid to obtain a 2-(alkyl)cycloalkenone represented by the following general formula (3) (hereinafter referred to merely as a "compound (3)"). Then, the thus obtained compound (3) is reacted with a malonic acid diester represented by the following general formula (4) (hereinafter referred to merely as a "compound (4)") in the presence of a base catalyst to obtain a compound (8) represented by the following general formula (8).

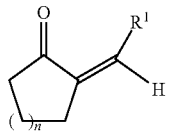
(2)

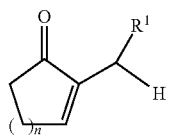
(3)

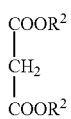
(4)

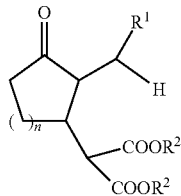
(8)

In the above general formulae (2) to (4) and (8), n, $R^1$ and $R^2$ are the same as defined above. In the general formulae (4) and (8), the two $R^2$ groups may be the same or different from each other.

The base catalyst used in the reaction between the compounds (3) and (4) is not particularly limited. Examples of the base catalyst include alkali metals such as sodium and potassium; and alkali metal alkoxides such as sodium alkoxides and potassium alkoxides. The amount of the base catalyst used in the reaction is preferably from 0.005 to 0.2 mol per 1 mol of the compound (3). The reaction between the compounds (3) and (4) is preferably carried out in a polar solvent such as alcohols. The reaction temperature is preferably from −10 to 30° C. and more preferably from 0 to 20° C.

The thus obtained compound (8) is then reacted with water to produce the compound (5). In the reaction, water is preferably added dropwise. The amount of water added is preferably from 1 to 3 mol per 1 mol of the compound (8) to be reacted therewith. The reaction temperature is preferably from 150 to 250° C.

[Method for Production of 5-Alkyl-5-alkanolide]

By using the compound (1) produced by the above production process as a raw material, it is possible to obtain a 5-alkyl-5-alkanolide represented by the following general formula (6) (hereinafter referred to merely as a "compound (6)"), which is useful as perfume materials or as physiologically active substances.

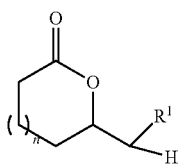
(6)

In the general formula (6), n and $R^1$ are the same as defined above.

More specifically, the compound (6) may be produced by the following method. First, the compound (1) is subjected to dehydration reaction to obtain the compound (2). The thus obtained compound (2) is subjected to isomerization reaction in the presence of an aqueous acid such as hydrochloric acid and hydrobromic acid in n-butanol under reflux to obtain the compound (3). Then, the thus obtained compound (3) is reduced with hydrogen in the presence of a catalyst such as Pd/C to obtain a compound (9) represented by the following general formula (9).

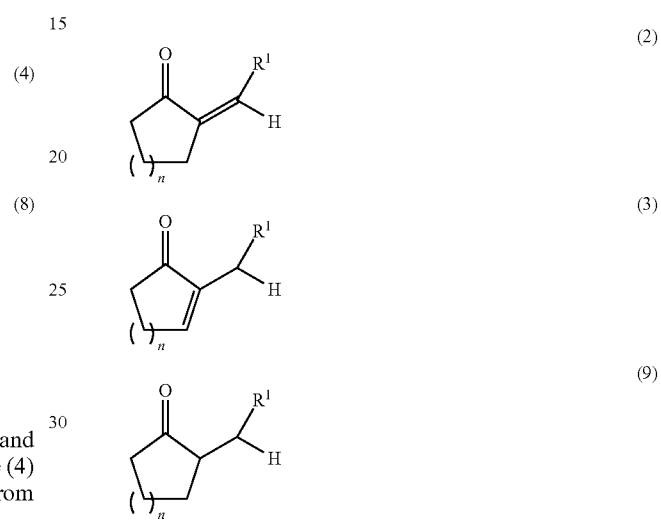

In the general formula (9), n and $R^1$ are the same as defined above.

The thus obtained compound (9) is then subjected to Baeyer-Villiger oxidation using an oxidizing agent such as peracetic acid as described, for example, in JP-A 9-104681 to thereby produce the compound (6).

EXAMPLES

Example 1

A 100 mL four-necked flask was charged with 16.6 g (0.92 mol) of water and 0.16 g (0.004 mol) of sodium hydroxide. After cooling the contents of the flask to 15° C. under stirring, a mixed solution containing 61.3 g (0.71 mol) of valeraldehyde (acid value: 1.5 mg-KOH/g) and 237.8 g (2.83 mol) of cyclopentanone, and 36.0 g of a sodium hydroxide aqueous solution (concentration of sodium hydroxide: 0.36% by mass) were added dropwise into the flask over 6 h. While dropping, the resulting reaction mixture was withdrawn from the flask at a rate 1.4 times the dropping rate, and introduced into a dropping funnel (separator) to separate the reaction mixture into an organic layer and a water layer. The water layer separated as a lower layer of the reaction mixture was returned to the flask. Whereas, the organic layer separated as an upper layer of the reaction mixture was collected every one hour, and each part of the organic layer collected every one hour was subjected to gas chromatography. After completion of the dropping, the reaction mixture in the flask was separated into the respective layers, and each of the thus separated organic and water layers was analyzed by gas chromatography. As a result, it was confirmed that the organic layer contained 3.06 g (0.036 mol) of valeraldehyde, 106.5 g (0.63 mol) of 2-(1-hydroxy-n-pentyl)cyclopentanone and 2.13 g (0.014 mol) of pentylidene cyclopentanone (conversion rate of valeraldehyde: 95.0%; yield: 89.9%).

On the other hand, it was confirmed that the organic layer withdrawn between the time at which one hour elapsed after initiation of the dropping and the time at which two hours elapsed after initiation of the dropping (between the 1st hour and the 2nd hour) contained 0.9% by mass of valeraldehyde and 32.4% by mass of 2-(1-hydroxy-n-pentyl)cyclopentanone, and the organic layer withdrawn between the time at which five hours elapsed after initiation of the dropping and the time at which six hours elapsed after initiation of the dropping (between the 5th hour and the 6th hour) contained 1.0% by mass of valeraldehyde and 32.6% by mass of 2-(1-hydroxy-n-pentyl)cyclopentanone. This showed that the reaction proceeded in a stable manner during the dropping. In addition since the amount of water contained in the water layer and the amount of sodium hydroxide after completion of the dropping were substantially identical to those initially charged, it was also confirmed that the amount of water dissolved in the organic layer and the amount of the base catalyst consumed by the reaction with valeric acid contained in the valeraldehyde were continuously supplied and compensated by the sodium hydroxide aqueous solution being dropped.

Example 2

A 200 mL four-necked flask was charged with 33.0 g (1.83 mol) of water and 0.64 g (0.02 mol) of sodium hydroxide. After cooling the contents of the flask to 5° C. under stirring, a mixed solution containing 123.6 g (1.44 mol) of valeraldehyde (acid value: 1.5 mg-KOH/g) and 482.2 g (5.73 mol) of cyclopentanone, and 56.4 g of a sodium hydroxide aqueous solution (concentration of sodium hydroxide: 0.22% by mass) were added dropwise into the flask over 6 h. While dropping, the resulting reaction mixture was withdrawn from the flask at a rate 1.7 times the dropping rate, and introduced into a dropping funnel to separate the reaction mixture into an organic layer and a water layer. The water layer separated as a lower layer of the reaction mixture was returned to the flask. Whereas, the organic layer separated as an upper layer of the reaction mixture was collected every 0.5 hour, and each part of the organic layer collected every 0.5 hour was subjected to gas chromatography. After completion of the dropping, the reaction mixture in the flask was separated into the respective layers, and each of the thus separated organic and water layers was analyzed by gas chromatography. As a result, it was confirmed that the organic layer contained 2.98 g (0.035 mol) of valeraldehyde, 213.4 g (1.25 mol) of 2-(1-hydroxy-n-pentyl)cyclopentanone and 4.19 g (0.028 mol) of pentylidene cyclopentanone, and the conversion rate of valeraldehyde and the yield of the aimed product were 97.6% and 89.3%, respectively.

In addition, it was confirmed that the composition of the organic layer withdrawn during an initial stage of dropping of the mixed solution (between the 1st hour and the 2nd hour) was substantially identical to the composition of the organic layer withdrawn during a late stage of dropping of the mixed solution (between the 5th hour and the 6th hour) similarly to Example 1, and the reaction therefore proceeded in a stable manner.

Example 3

A 200 mL four-necked flask was charged with 33.0 g (1.83 mol) of water and 0.64 g (0.02 mol) of sodium hydroxide. After cooling the contents of the flask to 5° C. under stirring, a mixed solution containing 123.2 g (1.43 mol) of valeraldehyde (acid value: 1.5 mg-KOH/g) and 361.8 g (4.30 mol) of cyclopentanone, and 47.9 g of a sodium hydroxide aqueous solution (concentration of sodium hydroxide: 0.27% by mass) were added dropwise into the flask over 6 h. While dropping, the resulting reaction mixture was withdrawn from the flask at a rate 1.9 times the dropping rate, and introduced into a dropping funnel to separate the reaction mixture into an organic layer and a water layer. The water layer separated as a lower layer of the reaction mixture was returned to the flask. Whereas, the organic layer separated as an upper layer of the reaction mixture was collected every 0.5 hour, and each part of the organic layer collected every 0.5 hour was subjected to gas chromatography. After completion of the dropping, the reaction mixture in the flask was separated into the respective layers, and each of the thus separated organic and water layers was analyzed by gas chromatography. As a result, it was confirmed that the organic layer contained 4.87 g (0.057 mol) of valeraldehyde, 211.8 g (1.24 mol) of 2-(1-hydroxy-n-pentyl)cyclopentanone and 4.20 g (0.028 mol) of pentylidene cyclopentanone, and the conversion rate of valeraldehyde and the yield of the aimed product were 96.0% and 88.9%, respectively.

In addition, it was confirmed that the composition of the organic layer withdrawn during an initial stage of dropping of the mixed solution (between the 1st hour and the 2nd hour) was substantially identical to the composition of the organic layer withdrawn during a late stage of dropping of the mixed solution (between the 5th hour and the 6th hour) similarly to Example 1, and the reaction therefore proceeded in a stable manner.

Example 4

A 200 mL four-necked flask was charged with 33.0 g (1.83 mol) of water and 0.63 g (0.02 mol) of sodium hydroxide. After cooling the contents of the flask to 5° C. under stirring, a mixed solution containing 123.2 g (1.43 mol) of valeraldehyde (acid value: 1.5 mg-KOH/g) and 241.2 g (2.87 mol) of cyclopentanone, and 35.5 g of a sodium hydroxide aqueous solution (concentration of sodium hydroxide: 0.37% by mass) were added dropwise into the flask over 6 h. While dropping, the resulting reaction mixture was withdrawn from the flask at a rate 2.1 times the dropping rate, and introduced into a dropping funnel to separate the reaction mixture into an organic layer and a water layer. The water layer separated as a lower layer of the reaction mixture was returned to the flask. Whereas, the organic layer separated as an upper layer of the reaction mixture was collected every 0.5 hour, and each part of the organic layer collected every 0.5 hour was subjected to gas chromatography. After completion of the dropping, the reaction mixture in the flask was separated into the respective layers, and each of the thus separated organic and water layers was analyzed by gas chromatography. As a result, it was confirmed that the organic layer contained 10.09 g (0.12 mol) of valeraldehyde, 191.7 g (1.13 mol) of 2-(1-hydroxy-n-pentyl)cyclopentanone and 5.94 g (0.039 mol) of pentylidene cyclopentanone, and the conversion rate of valeraldehyde and the yield of the aimed product were 91.8% and 81.5%, respectively.

In addition, it was confirmed that the composition of the organic layer withdrawn during an initial stage of dropping of the mixed solution (between the 1st hour and the 2nd hour) was substantially identical to the composition of the organic layer withdrawn during a late stage of dropping of the mixed solution (between the 5th hour and the 6th hour) similarly to Example 1, and the reaction therefore proceeded in a stable manner.

Example 5

A 100 mL four-necked flask was charged with 16.6 g (0.92 mol) of water and 0.16 g (0.004 mol) of sodium hydroxide. After cooling the contents of the flask to 15° C. under stirring, a mixed solution containing 165.3 g (1.92 mol) of valeraldehyde (acid value: 1.5 mg-KOH/g) and 646.4 g (7.68 mol) of cyclopentanone, and 95.1 g of a sodium hydroxide aqueous solution (concentration of sodium hydroxide: 0.35% by mass) were added dropwise into the flask over 16 h. While dropping, the resulting reaction mixture was withdrawn from the flask at a rate 1.4 times the dropping rate, and introduced into a dropping funnel to separate the reaction mixture into an organic layer and a water layer. The water layer separated as a lower layer of the reaction mixture was returned to the flask. Whereas, the organic layer separated as an upper layer of the reaction mixture was collected every 1 hour, and each part of the organic layer collected every 1 hour was subjected to gas chromatography. After completion of the dropping, the reaction mixture in the flask was separated into the respective layers, and each of the thus separated organic and water layers was analyzed by gas chromatography. As a result, it was confirmed that the organic layer contained 11.88 g (0.14 mol) of valeraldehyde, 278.1 g (1.63 mol) of 2-(1-hydroxy-n-pentyl)cyclopentanone and 5.8 g (0.038 mol) of pentylidene cyclopentanone, and the conversion rate of valeraldehyde and the yield of the aimed product were 92.8% and 87.1%, respectively.

The compositional ratios of the main components of the organic layer with time are shown in Table 1. As a result, as shown in Table 1, it was confirmed that even when the reaction was continuously carried out for the period as long as 16 h, the reaction still proceeded in a stable manner.

drawn from the flask at the same rate as the dropping rate, and introduced into a dropping funnel to separate the reaction mixture into an organic layer and a water layer. The water layer separated as a lower layer of the reaction mixture was returned to the flask. After completion of dropping the mixed solution, the reaction mixture in the flask was separated into the respective layers, and each of the thus separated and water layers was analyzed by gas chromatography. As a result, it was confirmed that the organic layer contained 2.10 g (0.024 mol) of valeraldehyde, 101.6 g (0.60 mol) of 2-(1-hydroxy-n-pentyl)cyclopentanone and 1.91 g (0.013 mol) of pentylidene cyclopentanone, and the conversion rate of valeraldehyde and the yield of the aimed product were 96.5% and 88.0%, respectively.

Comparative Example 1-2

A 200 mL four-necked flask was charged with 27.2 g of the water layer obtained in Comparative Example 1-1 and 27.9 g (1.55 mol) of water. After cooling the contents of the flask to 15° C. under stirring, a mixed solution containing 59.6 g (0.69 mol) of valeraldehyde (acid value: 1.5 mg-KOH/g) and 237.8 g (2.83 mol) of cyclopentanone was added dropwise into the flask over 2 h. While dropping, the resulting reaction mixture was withdrawn from the flask at the same rate as the dropping rate, and introduced into a dropping funnel to separate the reaction mixture into an organic layer and a water layer. The water layer separated as a lower layer of the reaction mixture was returned to the flask. After completion of dropping the mixed solution, the reaction mixture in the flask was separated into the respective layers, and each of the thus separated organic and water layers was analyzed by gas chromatography. As a result, it was confirmed that the organic layer contained 3.79 g (0.044 mol) of valeraldehyde, 98.3 g (0.58 mol) of 2-(1-hydroxy-n-pentyl)cyclopentanone and 1.62 g (0.011 mol) of pentylidene cyclopentanone, and the conversion rate

TABLE 1

| Reaction time | | 0-1 | 1-2 | 2.3 | 3-4 | 4-5 | 5-6 | 6-7 | 7-8 |
|---|---|---|---|---|---|---|---|---|---|
| Valeraldehyde | mass % | 1.5 | 1.4 | 1.5 | 1.3 | 1.5 | 1.5 | 1.1 | 1.3 |
| Cyclopentanone | mass % | 53.7 | 54.9 | 55.5 | 55.9 | 55.2 | 55.2 | 54.5 | 55.0 |
| Pentylidene cyclopentanone | mass % | 0.5 | 0.5 | 0.5 | 0.5 | 0.6 | 0.6 | 0.7 | 0.7 |
| 2-(1-Hydroxy-n-pentyl) cyclopentanone | mass % | 33.0 | 31.5 | 31.5 | 31.5 | 31.4 | 31.2 | 31.5 | 31.4 |
| Reaction time | | 8-9 | 9-10 | 10-11 | 11-12 | 12-13 | 13-14 | 14-15 | 15-16 |
| Valeraldehyde | mass % | 1.3 | 1.3 | 1.3 | 1.3 | 1.4 | 1.5 | 1.4 | 1.3 |
| Cyclopentanone | mass % | 54.4 | 54.9 | 55.1 | 54.9 | 54.5 | 55.2 | 55.2 | 55.0 |
| Pentylidene cyclopentanone | mass % | 0.6 | 0.6 | 0.6 | 0.7 | 0.7 | 0.8 | 0.7 | 0.7 |
| 2-(1-Hydroxy-n-pentyl) cyclopentanone | mass % | 31.7 | 31.6 | 31.4 | 31.2 | 31.2 | 30.8 | 31.2 | 31.2 |

Comparative Example 1-1

A 200 mL four-necked flask was charged with 50.0 g (2.78 mol) of water and 0.48 g (0.012 mol) of sodium hydroxide. After cooling the contents of the flask to 15° C. under stirring, a mixed solution containing 59.7 g (0.69 mol) of valeraldehyde (acid value: 1.5 mg-KOH/g) and 237.9 g (2.83 mol) of cyclopentanone was added dropwise into the flask over 2 h. While dropping, the resulting reaction mixture was withof valeraldehyde and the yield of the aimed product were 93.6% and 85.0%, respectively.

Comparative Example 1-3

A 200 mL four-necked flask was charged with 28.0 g of the water layer obtained in Comparative Example 1-2 and 28.2 g (1.56 mol) of water. After cooling the contents of the flask to 15° C. under stirring, a mixed solution containing 59.0 g (0.68 mol) of valeraldehyde (acid value: 1.5 mg-KOH/g) and 237.8 g (2.83 mol) of cyclopentanone was added dropwise into the flask over 2 h. While dropping, the resulting reaction mixture was withdrawn from the flask at the same rate as the dropping rate, and introduced into a dropping funnel to separate the reaction mixture into an organic layer and a water layer. The water layer separated as a lower layer of the reaction mixture was returned to the flask. After completion of dropping the mixed solution, the reaction mixture in the flask was separated into the respective layers, and each of the thus separated organic and water layers was analyzed by gas chromatography. As a result, it was confirmed that the organic layer contained 9.77 g (0.11 mol) of valeraldehyde, 85.8 g (0.50 mol) of 2-(1-hydroxy-n-pentyl)cyclopentanone and 1.14 g (0.008 mol) of pentylidene cyclopentanone, and the conversion rate of valeraldehyde and the yield of the aimed product were 83.4% and 74.8%, respectively.

Comparative Example 1-4

A 200 mL four-necked flask was charged with 27.7 g of the water layer obtained in Comparative Example 1-3 and 28.1 g (1.56 mol) of water. After cooling the contents of the flask to 15° C. under stirring, a mixed solution containing 59.0 g (0.68 mol) of valeraldehyde (acid value: 1.5 mg-KOH/g) and 237.8 g (2.83 mol) of cyclopentanone was added dropwise into the flask over 2 h. While dropping, the resulting reaction mixture was withdrawn from the flask at the same rate as the dropping rate, and introduced into a dropping funnel to separate the reaction mixture into an organic layer and a water layer. The water layer separated as a lower layer of the reaction mixture was returned to the flask. After completion of dropping the mixed solution, the reaction mixture in the flask was separated into the respective layers, and each of the thus separated organic and water layers was analyzed by gas chromatography. As a result, it was confirmed that the organic layer contained 43.5 g (0.51 mol) of valeraldehyde, 25.4 g (0.15 mol) of 2-(1-hydroxy-n-pentyl)cyclopentanone and 0.21 g (0.001 mol) of pentylidene cyclopentanone, and the conversion rate of valeraldehyde and the yield of the aimed product were 26.2% and 22.0%, respectively.

From the results of Examples 1 to 5, it was recognized that according the production process of the present invention, 2-(1-hydroxyalkyl)cycloalkanone was able to be produced with a high yield in a continuous manner. On the other hand, from the results of Comparative Examples 1-1 to 1-4, it was confirmed that in the case where the production process was carried out without the step of adding an additional amount of water containing the base catalyst to the reaction system in order to maintain a constant concentration of the base catalyst and/or a constant amount of water in the reaction system, the process failed to give good results.

Industrial Applicability

In accordance with the present invention, it was possible to continuously produce 2-(1-hydroxyalkyl)cycloalkanones while preventing reduction in yield of the aimed product. These compounds are useful as an intermediate product for synthesis of physiologically active substances and perfume materials.

The invention claimed is:

1. A process for producing a 2-(1-hydroxyalkyl) cycloalkanone by subjecting a cycloalkanone and an alkyl aldehyde to aldol condensation in the presence of water and a base catalyst, the process comprising:
   (i): continuously mixing the cycloalkanone and the alkyl aldehyde in the water and the base catalyst to form a reaction system and allow the cycloalkanone and alkyl aldehyde to react with each other;
   (ii): continuously withdrawing the reaction mixture produced in (i) out of the reaction system while allowing the reaction to proceed, wherein an amount of the reaction mixture withdrawn is from 1.2 to 2 times a total amount of the cycloalkanone and alkyl aldehyde added in terms of a volume ratio there between; and
   (iii): adding an additional amount of water containing the base catalyst to the reaction system to maintain a constant concentration of the base catalyst and/or a constant amount of water in the reaction system while allowing the reaction to proceed.

2. The process according to claim 1, further comprising: (iv) separating the reaction mixture withdrawn in (ii) into an organic layer and a water layer to reuse the water layer.

3. The process according to claim 2, further comprising (v) subjecting the organic layer separated in (iv) to distillation to recover the cycloalkanone contained in the organic layer and then reuse of the cycloalkanone in the reaction system.

4. The process according to claim 1, wherein the cycloalkanone is added in an amount of from 2 to 6 mol per 1 mol of the alkyl aldehyde added.

5. The process according to claim 1, wherein an amount of the reaction mixture withdrawn is from 1.4 to 1.9 times a total amount of the cycloalkanone and alkyl aldehyde added in terms of a volume ratio there between.

6. The process according to claim 1, wherein the reaction in (i) is carried out at a temperature of from −5 to 40° C.

7. The process according to claim 1, wherein the 2-(1-hydroxyalkyl) cycloalkanone is a compound of formula (1):

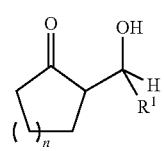

(1)

wherein n is an integer of 1 or 2; and $R^1$ is a hydrogen atom or an alkyl group having 1 to 8 carbon atoms.

* * * * *